United States Patent [19]

Konishi

[11] Patent Number: 4,985,254

[45] Date of Patent: Jan. 15, 1991

[54] METHOD OF TREATING ISCHEMIC DISEASES

[75] Inventor: Jin-emon Konishi, Hyogo, Japan

[73] Assignee: Nippon Zoki Pharmaceutical Co., Ltd., Osaka, Japan

[21] Appl. No.: 266,758

[22] Filed: Nov. 3, 1988

[30] Foreign Application Priority Data

Nov. 6, 1987 [JP] Japan .................. 62-281764

[51] Int. Cl.$^5$ ...................... A61K 35/12; A61K 35/36
[52] U.S. Cl. .................... 424/520; 424/574;
424/558; 424/559; 424/557; 424/553; 424/548;
424/563; 424/568; 424/570; 424/529; 424/573
[58] Field of Search ..................... 424/95, 520, 574

[56] References Cited

FOREIGN PATENT DOCUMENTS 3101515 9/1978 Japan ........................... 424/95
9118711 7/1984 Japan ........................... 424/95

OTHER PUBLICATIONS

Takeuchi et al., "Changes in Peripheral Blood Flow, Hyperalgesia and Swelling of Carrageenin-Induced Hind Paw Edena in Rats, and Effect of Neurotropin", J. Pharm. Sci., vol. 76 (11), Nov. 1987, p. S320.

Primary Examiner—Jacqueline Stone
Assistant Examiner—Jean Witz
Attorney, Agent, or Firm—Armstrong, Nikaido, Marmelstein, Kubovcik & Murray

[57] ABSTRACT

The present invention relates to physiologically active substances extracted from infected tissues inoculated with a poxvirus. The substances of the present invention have excellent actions to improve blood flow and recover functions of diseased tissues, thus are useful as drugs for various diseases caused by blood flow disorders.

3 Claims, No Drawings

METHOD OF TREATING ISCHEMIC DISEASES

BACKGROUND OF THE INVENTION

The present invention relates to physiologically active substances extracted from infected tissues and pharmaceutical compositions containing them.

Blood flow disorders are caused by various factors, for example, organic diseases of blood vessels such as arteriosclerosis, exposure to cold, physical and mental stresses, certain drugs and the like, and consequently tissues or organs fall into a state of ischemia. Several symptoms such as functional disorders of tissues or organs, feeling cold in foot and arms, numbness, pain and hypesthesia are presented. As a result of long continuance of this ischemia state, local tissues fall into atrophy, degeneration and necrosis finally.

As increasing aging population, many patients, especially old patients, often suffer from the said symptoms such as numbness, pain, functional troubles and the like. Therefore, it has been desired to develop drugs which can improve blood flow at diseased tissues and recover functions of such tissues as well as having greater safety without any side effects.

As a result of investigations for physiologically active substances extracted from infected tissues and produced by inoculation with a poxvirus to animal tissues, organs or cultured cells. The substances have been found having excellent action to improve blood flow and recover functions of diseased tissues as well as a process for the preparation thereof.

An object of the present invention is to provide novel physiologically active substances extracted from infected tissues. Another object of the invention is to provide pharmaceutical compositions containing the physiologically active substances.

DETAILED DESCRIPTION OF THE INVENTION

The present invention thus provides a process for preparing the physiologically active substances extracting from infected tissues inoculated with a poxvirus; deproteinizing the extract; mixing the deprotenized extraction with an adsorbent; eluting the adsorbed material from adsorbent; and fractionating the eluted material according to molecular weight. That according the process of the invention:

(1) Infected tissues are homogenized with an extraction medium, and tissue fragments are removed.

(2) Extracted solution thus obtained is subjected to treatment to remove proteins.

(3) An adsorbent is added to the deproteinized solution, and then the material adsorbed onto the adsorbent is eluted.

(4) The eluted material is further fractionated on molecular weight basis to give the substances of the present invention.

The term "infected tissues" as used in this specification is defined as meaning: animal tissues, organs or cultured cells inoculated or infected with a poxvirus.

A poxvirus, for example, orthopoxvirus such as vaccinia virus, cowpox virus, variola virus, infectious ectromelia virus or monkeypox virus, parapoxvirus such as orf virus, paravaccinia virus or bovine papular stomatitis virus, capricopoxvirus such as sheeppox virus, goatpox virus or lumpy skin disease virus, avipoxvirus such as fowlpox virus or hare fibroma virus, leporipoxvirus such as rabbit myxoma virus or rabbit fibroma virus, swinepoxvirus, Yaba monkey tumor virus or Tarapox virus, can be used.

To obtain the infected tissues, various kinds of animals or birds can be utilized, for example, rabbit, sheep, goat, pig, cow, horse, monkey, hamster, guinea pig, rat, mouse or hen can be employed. The animal or bird can be selected according to a specie of poxvirus and other conditions. Also any kind of cultured cell, in which the selected poxvirus can multiply, is available, for example, cultured cell or tumor cell of kidney, skin, lung, testis, liver, muscle, adrenal, thyroid gland, brain, nerve cell or blood cell of rabbit, sheep, goat, pig, cow, horse, monkey, hamster, guinea pig, rat, mouse, hen or their embryo, cultured cell derived from human such as Hela cell, or decidua of the hatching egg can be employed.

The infected tissues are collected under aseptic conditions and ground to as small a size as possible. An extraction medium is added to the ground material which is then homogenized. As an extraction medium, distilled water, physiological saline, weakly acidic or basic buffer etc. may be used, and if desired, a stabilizer such as glycerin, a disinfectant or preservative such as phenol, or an inorganic salt such as sodium chloride, potassium chloride or magnesium chloride can be added to the medium. At that time, the extraction can be facilitated by a procedure to disintegrate cell tissues, such as freeze-thaw extraction, sonication or treatment with a detergent or an enzyme dissolving cell membrane.

The resulting emulsion is filtered or centrifuged to remove tissue fragments. The filtrate or supernatant is deproteinized which can be carried out according to a known method, for example, heating, sonication, treatment with a protein-denaturant such as an acid, a base, urea, guanidine, an organic solvent or a detergent, isoelectric point precipitation or salting-out technique. Subsequently, the denatured proteins thereby precipitated are removed by filtration using a filter paper such as cellulose or nitrocellulose, a glass filter, sellaite, Seitz's filter etc., ultrafiltration, gel filtration, ion-exchange chromatography or centrifugation.

The resulting extract containing the active substances is acidified, preferably to pH 3.5–5.5, by addition of an acid such as hydrochloric acid, sulfuric acid or hydrobromic acid, and then subjected to adsorption to an adsorbent such as active carbon, kaolin or an ion-exchange resin. The adsorbent can be added to the extracted solution and it is stirred, or the extracted solution can be passed through a column of the adsorbent.

To elute the material containing the active substances of the present invention, a basic solution is added to the absorbent, preferably adjusting the suspension to pH 9–12, and then the mixture is incubated or stirred at room temperature or at a suitable temperature above room temperature by heating. The elution is achieved by removing the absorbent according to a known method such as filtration or centrifugation. After the eluate is adjusted to near neutral by addition of an acid, fractionation based on molecular weight such as ultrafiltration or gel filtration is carried out to give the active substances of the present invention.

EXAMPLE

The following examples, which are illustrative only and not intended to limit the scope of the invention, describe the preparation of the physiologically active substances of the present invention.

EXAMPLE 1

Vaccinia virus was inoculated to the skin of healthy adult rabbit. The inflamed skin was cut off under aseptic conditions and well ground. Aqueous phenol solution was added to this ground material and subjected to homogenization, and the emulsion was filtered by centrifugation. The resulting filtrate was adjusted to pH 4.5–5.5, and then heated in a stream of 100° C. steam. After removing proteins thereby precipitated by filtration, the filtrate was adjusted to pH 8.5–10.0 by addition of sodium hydroxide, heated at 100° C. and filtered. The filtrate was adjusted to pH 5.0 and 7.5% active carbon was added thereto. After stirring for 4 hrs, the suspension was filtered. Water was added to the resulting active carbon and the suspension was adjusted to pH 9.5 by addition of sodium hydroxide. The extraction procedure was carried out by stirring for 1.5 hrs at 60° C. The suspension was filtered to remove the active carbon. The filtrate was adjusted to near neutral pH, e.g. pH 6.5–8.5, by addition of hydrochloric acid and concentrated to dryness under reduced pressure. The residue was dissolved in distilled water and any insoluble matter was removed by filtration. Subsequently, the solution was filtered through a ultrafiltration membrane eliminating substances molecular weight of which is more than 5,000. To the remaining solution concentrated to small amount, distilled water was added and it was filtrated again. The procedure was repeated several times. Next the resulting filtrate, which contains substances of molecular weight less than 5,000, was subjected to ultrafiltration again using membrane eliminating substances molecular weight of which is more than 500 in the same manner as mentioned above to give the substances of the present invention, which did not pass the membrane.

EXAMPLE 2

The extract prepared in the same deproteinizing process as Example 1 was adjusted to pH 3.5 and 15% active carbon was added thereto. After stirring for 5 hrs, the suspension was filtered. To the resulting active carbon, aqueous solution of sodium hydroxide (about pH 11) was added and the suspension was stirred for 3 hrs at 45° C. The active carbon was removed by filtration. The filtrate was neutralized and subjected to the ultrafiltration procedures, which was carried out in the same manner as Example 1, to give the physiologically active substances of the present invention.

The substances of the invention thus obtained was concentrated to dryness under reduced pressure. As a result of weighing the dried substances, the yield of the substances of the present invention is 0.5–1.0 g when 1 kg of infected skin-tissues of mature rabbit are employed.

The physical and chemical properties of the physiologically active substances obtained in the above examples are as follows.
(1) Appearance:
  Pale yellowish brown and hygroscopic powder.
(2) Solubility:
  Soluble in water, methanol and acetone.
  Insoluble in benzene and ether.
(3) Acidity:
  The pH of aqueous solution thereof is pH 6.5–7.5.
(4) Molecular weight: 500–5,000
(5) Ultraviolet adsorption: $\lambda max = 265-275$ nm.
(6) Color reaction:
  Positive; amino acid, sugar, phosphorus.
  Negative; protein, phenol.

The following descriptions serve to illustrative pharmaceutical studies of the substances of the present invention.

(1) Toxicity Test

The physiologically active substances of the present invention were administered to male and female of mice and rats orally, subcutaneously, intraperitoneally and intravenously to carry out acute toxicity tests. $LD_{50}$ of the substances of this invention was more than 5,000 mg/kg at any route of administrations independently of species of animals and differences between the sexes.

As a result of subacute toxicity tests, no abnormality was observed at any organs. The reproduction tests showed no effect on pregnant animal, fetus, newborn and reproductivity of offspring ($F_1$).

(2) Action of Improving Blood Flow

The physiologically active substances of the present invention were orally administered (50 to 400 mg/kg of body weight) to Wistar-strain male rats weighing about 200 g. After 1 hour, 0.1 ml of 0.2% carrageenin was subcutaneously injected into the right hind paw. The skin temperature of the hind paw was observed thermographycally until 48 hours after carrageenin administration.

45 minutes to 3 hours after the carrageenin injection, the thermography showed the lowering of skin temperature. The substances of the present invention dose-dependently elevated the skin temperature lowered by carrageenin. These thermographic studies demonstrated the substances of the present invention have the normalizing action in the skin temperature lowered abnormally, evidently indicating the improvement of blood flow.

(3) Clinical Study

The pharmaceutical compositions containing the substances of the present invention as an active ingredient were administered to patients suffering from numbness, pain, cold feeling in foot and arms, paresthesia and the like, for example, patients with Raynaud syndrome, diabetic neuropathy and subacute myelo-optico neuropathy (SMON). In case of preparations for injections, 3 to 12 mg daily of the substances of the present invention dissolved in physiologically saline solution were intravenously administered to the said patients for a day to 2 weeks. Symptoms such as numbness, pain, cold feeling in feet and arms and paresthesia were apparently cured by treatment with the substances of the invention. The substances were significantly superior to placebo group in both general improvement rate and overall clinical efficacy, for example, the rate of moderate to marked improvement was about 70%, and the rate of more than slightly improvement was more than 90% in case of treatment with the substances of the present invention.

Furthermore, in the said clinical trials, severe side effect was not found at all, and few side effects such as sleeplessness, sweating, thirst and gastrointestinal disorders were observed.

As shown by the above-mentioned results, the physiologically active substances of the present invention have excellent pharmacological effects improving blood flow of various tissues falling into a state of ischemia without overloading the heart, and consequently normalizing functions of diseased tissues. The substances of this invention also other pharmacological effects such as increasing cerebral glucose utilization and preventing aging of cerebral cells. Therefore, the substances of this invention are not only useful as drugs for various diseases caused by blood flow disorders, for example, health hazard due to vibration, arteriosclerosis obliterans, thromboangiitis obliterans, progressive muscular atrophy, cerebrovascular diseases, such as cerebral embolism, cerebral apoplexy, cerebral arteriosclerosis and dementia, periarteritis nodosa, systemic lupus erythematosus, rheumatoid arthritis, aoritis syndrome, Raynaud syndrome, diabetic neuropathy, subacute myelo-optico neuropathy, ischemic neuropathy, frostbite, ear noises, hearing loss and occlusion of retinal artery, but also drugs to cure or mitigate concomitant symptoms with the said diseases such as cold feeling, numbness, pain, hypesthesia, functional troubles, atrophy, necrosis and the like. The substances of the invention have low toxicity and great safety, so that their long-term continuous administration and oral use are possible.

The substances of the present invention can be made into pharmaceutical compositions by combination with appropriate medicinal carriers or diluents, and can be formulated into preparations in solid, semisolid, liquid or gaseous form such as tablets, capsules, powders, granules, solutions and suppositories in usual ways for oral or parenteral administrations.

In pharmaceutical dosage forms, the substances of the present invention can be used in the form of their pharmaceutically acceptable salts, and also can be used alone or in appropriate association, as well as in combination with other pharmaceutically active components.

In case of oral preparations, the substances can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or calcium carboxymethylcellulose; with lubricants such as talc or magnesium stearate; and if desired, with diluents, buffering agents, moistening agents, preservatives and flavoring agents.

The substances of the present invention can be formulated into a preparations for injections by dissolving, suspending or emulsifying in aqueous or nonaqueous solvent, such as distilled water for injection, physiologically saline solution, 5-20% glucose aqueous solution, vegetable oil, synthetic aliphatic acid glycerides, esters of higher aliphatic acid or propylene glycol.

Furthermore, the substances of the invention can be made into a suppository by mixing with a variety of bases, e.g. emulsifying base or water-soluble base, and also can be made into inhalations or aerosol preparations.

The desirable dose of the substances of the present invention varies with the subject, form of the drug, method and period of administration. However, in order to obtain desirable effects, generally it is recommended to administer orally 1 to 100 mg, preferably 4 to 400 mg daily.

In case of parenteral administrations e.g. injections, doses of the substances in the order of one tenth to one third of the above dose are preferable as daily doses.

Some prescriptions of the pharmaceutical compositions are shown below as examples which contain the substances of the present invention as an active ingredient.

| Prescription example 1 (tablet) | |
| --- | --- |
| Component | Content in a tablet (mg) |
| substances of this invention | 4 |
| lactose | 106 |
| crystalline cellulose | 40 |
| calcium carboxymethylcellulose | 20 |
| magnesium stearate | 10 |
| Total | 180 mg |

| Prescription example 2 (capsule) | |
| --- | --- |
| Component | Content in a capsule (mg) |
| substances of this invention | 10 |
| lactose | 200 |
| talc | 40 |
| Total | 250 mg |

| Prescription example 3 (injection) | |
| --- | --- |
| Component | Content in an ampule (mg) |
| substances of this invention | 1 |
| sodium chloride | proper amount |
| distilled water for injection | proper amount |
| Total | 1 ml |

What is claimed is:

1. A method for treating Raynaud's disease which comprises administering to an animal in need of such treatment an effective amount of a substance prepared by extracting infected tissue inoculated with a poxvirus, deproteinizing the extract, mixing the deproteinized extract with an adsorbent, eluting the adsorbed material from the adsorbent and fractionation the eluate, said substance being a hygroscopic powder, pale yellowish brown in appearance, soluble in water methanol and acetone and insoluble in benzene and ether, having a molecular weight of 500-5,000 and ultraviolet adsorption of $\lambda$ max=265-275 nm, and which gives a positive color reaction for amino acid, sugar and phosphorus, and a negative color reaction for protein and phenol.

2. A method for treating diabetic neuropathy which comprises administering to an animal in need of such treatment an effective amount of a substance prepared by extracting infected tissue inoculated with a poxvirus, deproteinizing the extract, mixing the deproteinized extract with an adsorbent, eluting the adsorbed material from the adsorbent and fractionation the eluate, said substance being a hygroscopic powder, pale yellowish brown in appearance, soluble in water methanol and acetone and insoluble in benzene and ether, having a molecular weight of 500-5,000 and ultraviolet adsorption of $\lambda$ max=265-275 nm, and which gives a positive color reaction for amino acid, sugar and phosphorus, and a negative color reaction for protein and phenol.

3. A method for treating subacute myelo-opticaneuropathy which comprises administering to an animal in need of such treatment an effective amount of a substance prepared by extracting infected tissue inoculated with a poxvirus, deproteinizing the extract, mixing the deproteinized extract with an adsorbent, eluting the adsorbed material from the adsorbent and fractionation the eluate, said substance being a hygroscopic powder, pale yellowish brown in appearance, soluble in water methanol and acetone and insoluble in benzene and ether, having a molecular weight of 500-5,000 and ultraviolet adsorption of $\lambda$ max=265-275 nm, and which gives a positive color reaction for amino acid, sugar and phosphorus, and a negative color reaction for protein and phenol.

* * * * *